United States Patent [19]

Przuntek et al.

[11] Patent Number: 5,026,357
[45] Date of Patent: Jun. 25, 1991

[54] INJECTION DEVICE

[75] Inventors: Horst Przuntek, Bochum; Simon Bittkau, Würzburg, both of Fed. Rep. of Germany

[73] Assignee: Schering AG, Berlin, Fed. Rep. of Germany

[21] Appl. No.: 326,707

[22] Filed: Mar. 21, 1989

Related U.S. Application Data

Continuation-in-part of PCT EP87/00535 filed Sept. 18, 1987.

[30] Foreign Application Priority Data

Sep. 22, 1986 [DE] Fed. Rep. of Germany ... 8625574[U]
Sep. 22, 1986 [DE] Fed. Rep. of Germany ... 8625575[U]

[51] Int. Cl.$^5$ .............................................. A61M 5/00
[52] U.S. Cl. ....................................... 604/258; 604/93
[58] Field of Search ............... 604/130, 187, 239, 242, 604/243, 258, 261, 94, 93, 173, 174, 179, 180

[56] References Cited

U.S. PATENT DOCUMENTS

| 2,718,887 | 9/1955 | Block | 604/187 |
|---|---|---|---|
| 3,874,380 | 4/1975 | Baum | 604/94 |
| 3,964,482 | 6/1990 | Gerstel et al. | 128/260 |
| 4,046,479 | 9/1977 | Paley | 604/242 |
| 4,159,720 | 7/1979 | Burton | 604/891.1 |

FOREIGN PATENT DOCUMENTS

| 1907296 | 9/1969 | Fed. Rep. of Germany | 604/258 |
|---|---|---|---|
| 3035009 | 3/1982 | Fed. Rep. of Germany . | |
| 1133709 | 4/1957 | France . | |
| 1142769 | 9/1957 | France . | |

*Primary Examiner*—Stephen C. Pellegrino
*Assistant Examiner*—Michael Rafa
*Attorney, Agent, or Firm*—Nils H. Ljungman

[57] ABSTRACT

The invention relates to a medicament injection device in which the material to be injected can be distributed through injection points over a large area surface, whereby simultaneously the device can be easily secured at the injection points and can lie relatively flush with the body without taking up a great deal of space. A mounting support is provided on which several cannulae are held spaced from one another, which are connected with a supply conduit and whose longitudinal axes, when the device is in a flat position, extend parallel to one another.

20 Claims, 1 Drawing Sheet

INJECTION DEVICE

CROSS REFERENCE TO RELATED APPLICATIONS

This application is a continuation-in-part of International Application No. PCT/EP87/00535 filed on Sept. 18, 1987, in which the U.S. was a designated state, which claims priority from Federal Republic of Germany Patent Application Nos. G 86 25 575.4 and G 86 25 574.6 both filed on Sept. 22, 1986.

BACKGROUND OF THE INVENTION

1. Field of the Invention

This invention relates to injection devices for the dispensation of medicaments and, more particularly, to such devices that are self-dispensing continuously, periodically or at different intervals.

2. Description of the Prior Art

It is known to use injection needles for continuous or periodic subcutaneous or intramuscular introduction of aqueous, oil-based or other liquid-based medicaments into body tissue. These injection needles can be connected to a mechanical or automatic dosage device by means of a tube of material which is tissue compatible and is substantially inert with respect to the medicament solution.

For the treatment of certain illnesses such as Parkinson's disease, among others, a continuous or periodic supply of medicament is desired because, in this manner, uniformity of dispensation of the active ingredient or ingredients of the medicament solution may be attained in the patient's body. In order to allow the patient both freedom of movement and also the avoidance of the inconvenience of stationary treatment as well as mistakes in introduction, it is conventional to use an electronic dosage pump which is carried on or affixed to the body. The pump releases the medicament via a tubular duct through an injection cannula fixed in the subcutaneous or muscle tissue, but this can create a problem. For example, medicament concentrations at the entry point into the body tissue are higher than may be needed. The increased medicament concentrations arising at the injection spot can, depending on the chemistry of the medicament as well as its concentration, lead to local irritation and inflammatory types of conditions which in extreme cases can make it necessary to end the beneficial therapy.

U.S. Pat. No. 4,159,720 describes an apparatus which introduces the medicament solution into the body from a reservoir fastened on the skin through a wick of silk or medical sewing material. This method has the disadvantage that the dosage rate is predetermined by the wick surface area and its absorption characteristics. Therefore, it is unlikely that a prescribed dosage rate over the course of the day can be realized. Furthermore, tissue compatibility of the wick material can be a problem in certain cases. To the same effect is Australian Patent No. 253,426 which is directed to a syringe having cannulae extending in opposed directions from a hub. Again, the concentration problem and resultant irritation are not obviated.

In Federal Republic of Germany Laid Open Patent Application No. DE-OS 30 35 009, an injection head is disclosed. It is provided with supports for receiving injection needles. This is, however, envisaged as part of an injection tip for heat spot formation. Because of the size and shape and the constructional details of the injection head and the support for receiving the injection tip, this device is not suitable to be worn on the body for prolonged periods of time after fixing in the desired injection position.

In French Patent No. 11 42 769, an injection needle is described which has lateral openings so that the medicament to be injected is divided in the tissue along the needle. In spite of the division into different effective depths, it does not address the problem of undesired concentrations at the entry point or the need for spreading the medicament laterally along the surface of the patient's body.

French Patent No. 11 33 709 describes an apparatus for reflex therapy which has a box-like reservoir for a medicament, whereby a plurality of parallel injection needles extend from the base of the reservoir and are connected with the latter via capillaries so that only drops are introduced onto the skin area. Again, this apparatus is not suitable for fixing on the body for anything but the briefest periods.

Thus, this invention directly addresses the problem of providing an injection device for scheduled self-injections of medication which can be easily fixed on the body and which obviates the concentration centers of prior art devices.

OBJECTS OF THE INVENTION

An object of the invention is the provision of an injection device which facilitates a predetermined distribution of medicaments over a wider lateral area of the patient's body with a plurality of injection points, and, thereby, without contributing to any unnecessary discomfiture of cumbersome or awkward apparatuses.

Another object of the invention provides for an injection device having such structure that tissue irritation and inflammation produced by high medicament concentrations at the entry point is thereby avoided or minimized.

SUMMARY OF THE INVENTION

The aforementioned objects are attainable by providing an injection device with a hollow support and duct member for the transportation of medicaments from a pump, all of which are attachable to a patient's body. In its flat position, the longitudinal axis of the support and duct member is substantially parallel with an outer body-contacting surface containing two or more orifices, the longitudinal axes of which are transverse and, advantageously, perpendicular to the longitudinal axis of the support and duct member. An equal number of substantially parallel cannulae communicate with such orifices. The distal portion of each cannula is designed to penetrate into the patient's body. Advantageously, cannula can be provided with one or more openings which are transverse,; e.g., perpendicular to the longitudinal axis of such cannula.

This structure increases the number of entry points into the patient's body while at the same time limiting the area of the patient's body encumbrance covered by such a device.

Advantageously, the injection device support member is flexible and can be shaped by hand to lay flat along the uneven contours of the patient's body.

The injection device can be applied in an easy manner because of the parallel longitudinal axes of the cannulae, which may lie in one or more vertical planes. That is, the support member may take any shape, e.g., it may be rectilinear, angular, regularly or irregularly curved-shaped, elliptical, or advantageously, round or circular.

A particularly simple and very useful construction is achieved in that a tubular duct arrangement is provided which forms the support and supply duct, the tubular axis or the tubular axes of the duct arrangement lying in one plane in its flat position and connected with the cannulae which are arranged on one side of this plane and perpendicular thereto, but the longitudinal axes of the cannulae are not all coplanar in such a case. It is advantageous if this tubular duct arrangement is a rigid tubular duct ring; i.e., rigid enough to support its own weight but nevertheless shapeable to cover the desired area of the patient's body. Such a tubular duct ring fulfills in an ideal manner the requirement of being capable of being well fixed and, without great space requirement, being able to lie flush with the body.

The support member can be made up employing, for example, a clear flexible plastic that is readily hand-shapeable by the patient for fitting to the patient's body. A tangential connection spigot is provided for this tubular duct ring. In particular, the cannulae are arranged at a uniform distance from one another if this is what is called for by the treating physician or the exigencies of the treatment desired or needed.

If, in addition to the distribution over the surface still an additional distribution in the depth is desired, any such cannulae may be provided with a closed cannula point and with one or more lateral exit openings running transverse or substantially perpendicular to the longitudinal axis or axes of any such cannulae.

So that the injection device according to the invention can be easily used by the patient himself, a handle, for example, one that is curved or ergonomically shaped, can advantageously be mounted on the rigid holder supporting the cannulae.

BRIEF DESCRIPTION OF THE DRAWINGS

A preferred embodiment of the invention is described by way of example with reference to the drawings in which.

DESCRIPTION OF THE PREFERRED EMBODIMENT

Figure 1:
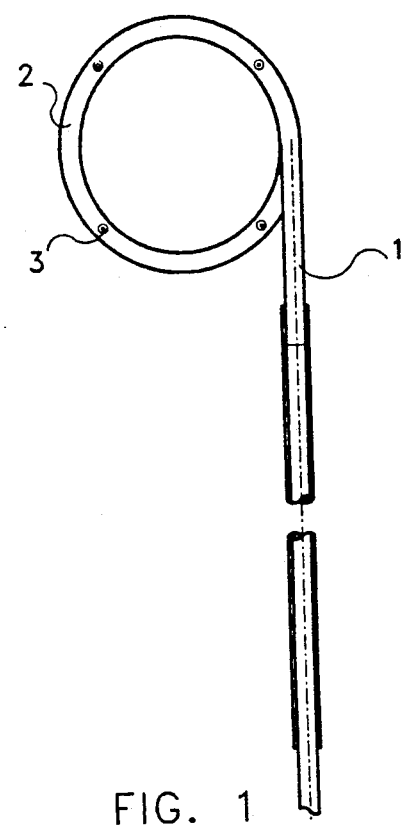
FIG. 1 is a plan view of a tubular duct ring.

In the drawings, a tubular duct ring 2 is illustrated. This tubular duct ring 2 has a tangential connection spigot 1 which can, for example, be connected with a Teflon tube to which a Luer-Look connection can be fitted.

Figure 3:
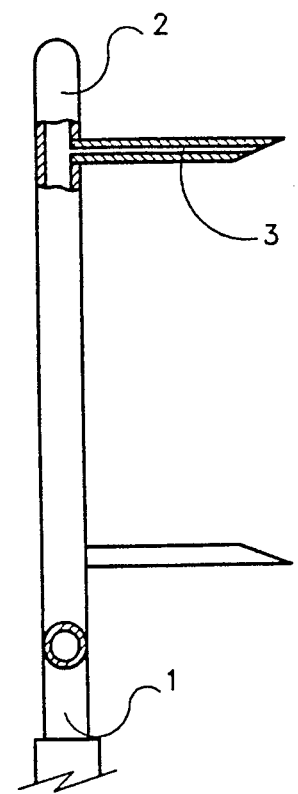
FIG. 3 is a schematic, partially sectioned side view.
Figure 2:
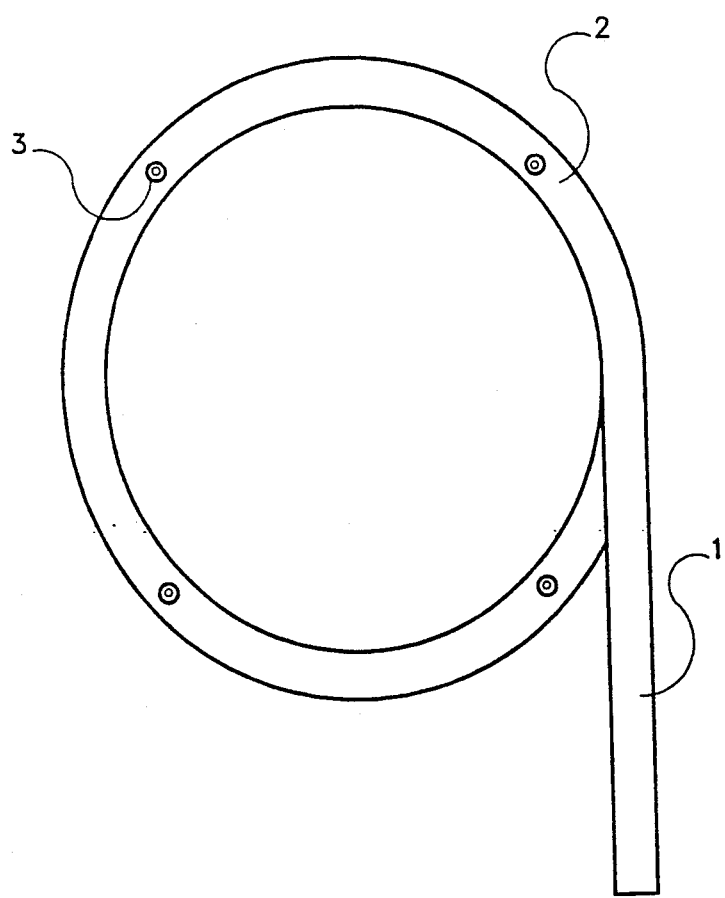
FIG. 2 is an enlarged view of the tubular duct ring from below.

As shown particularly in FIG. 3, several cannulae 3 extend perpendicular to the horizontal plane of the tubular duct ring 2 on one side, and these cannulae are in communication with the tubular duct ring. The axes of the cannulae 3 extend parallel to one another and in the same direction.

A preferred embodiment has the features that the cylindrical hollow body comprises an annular tube with an outer diameter of 20 millimeters ("mm"). The tube's inner diameter is about 1 mm, while the tube's outside diameter is about 1.5 mm. Perpendicular to the plane of the annulus, four injection cannulae are mounted on the same side parallel and equidistant from one another with a passage or inside diameter of 0.2 mm and an outer diameter of 0.45 mm. The annular tube also has, tangential and parallel to the annular plane, a straight connection tube of 16 mm length with the same tubular cross section as the annular tube. Resulting from the arrangement of the injection cannulae on an annular tube, this injection head can be readily and firmly fixed to the body after insertion of the cannulae at the suitable injection points by suitable means (physiologically compatible cross-plaster bandage or the like).

The manner of use of the injection needle in accordance with the invention is as follows:

The entire system (dosage device, supply tube and injection device) is filled with the medicament solution without any air bubbles and the cannulae are inserted in the body tissue at the desired position so that the annular tube lies on the skin. The injection device is then secured to the body by physiologically acceptable plasters and the like, and the dosage device is set into operation.

In summing up, one aspect of the invention resides in an injection device with several cannulae 3, held spaced apart from one another in a rigid mounting support and connected with a supply duct. The longitudinal axes of the cannulae are arranged parallel to one another. A tubular duct arrangement 2 forms the rigid mounting support and supply duct. The tubular axis or tubular axes of the duct arrangement lie in a plane A—A and connect the camnulae 3, which are arranged on one side of the plane and are perpendicular to it.

Another aspect of the invention resides in that the tubular duct arrangement is a tubular duct ring 2.

Still another aspect of the invention resides in that there is a tangential connection spigot 1 for the tubular duct ring 2.

Still yet another aspect of the invention resides in that the cannulae 3 are arranged equally spaced from one another.

And still yet another aspect of the invention resides in that the cannulae have a closed cannula tip and several lateral exit openings.

A further aspect of the invention resides in that a handle is mounted on the rigid holder.

The invention as described hereinabove in the text of preferred embodiments is not to be taken as limited to all of the provided details thereof, since modifications and variations thereof may be made without departing from the spirit and scope of the invention.

What is claimed is:

1. An injection device for the dispensation of medicaments comprising:
    a hollow support and duct member having a longitudinal axis which is substantially parallel with an outer body-contacting surface containing orifices;
    said hollow support and duct member being flexible for conforming to contours of the body of a user and lying against the contours;
    said orifices having longitudinal axes which are transverse to the longitudinal axis of the support and duct member;
    said orifices communicating with the duct of said member; and
    cannulae communicating with said orifices.

2. An injection device according to claim 1, wherein there are more than two orifices and an equal number of cannulae.

3. An injection device according to claim 2, wherein the longitudinal axes of the cannulae do not all lie in the same plane.

4. An injection device according to claim 2, wherein the longitudinal axis of the support and duct member is nonrectilinear.

5. An injection device according to claim 2, wherein the support and duct member is arcuate.

6. An injection device according to claim 2, wherein the cannulae are substantially evenly spaced one from the other.

7. An injection device according to claim 2, wherein the support and duct member is ring-shaped and the cannulae are substantially evenly spaced.

8. An injection device according to claim 2, wherein at least one cannula is closed at the end remote from its corresponding orifice and such cannula contains at least one medicament-transporting duct transverse to its longitudinal axis.

9. An injection device according to claim 2, wherein the support and duct member is provided with a longitudinal connection for a medicament spigot.

10. An injection device according to claim 2, wherein the support and duct member has rigidity to support its own weight.

11. An injection device according to claim 2, wherein the support and duct member is ring-shaped and the longitudinal axis of the cannulae are substantially perpendicular to the longitudinal axis of the support and duct member.

12. An injection device according to claim 11, wherein at least one of the cannulae is closed at the end remote from its corresponding orifice and each such cannulae contains at least one medicament-transporting duct substantially perpendicular to the longitudinal axis of such cannula.

13. An injection device according to claim 11, wherein the support and duct member is tangentially connected to a spigot.

14. An injection device according to claim 11, wherein the orifices are substantially evenly spaced.

15. An injection device according to claim 12, wherein there are at least two medicament-transporting ducts.

16. An injection device according to claim 15, wherein the support and duct member is for affixing by affixing means to an area to receive an injection, the affixing means comprising physiological compatible cross-plaster bandages.

17. An injection device according to claim 16, wherein the support and duct member and the longitudinal connection are configured to have a low-profile.

18. An injection device for the substantially continuous dispensation of medicaments comprising:
   a hollow support and duct member having a longitudinal axis which is substantially parallel with an outer body-contacting surface containing orifices;
   said hollow support and duct member being flexible for conforming to contours of the body to lay against the contours;
   said orifices having longitudinal axes which are transverse to the longitudinal axis of said support and duct member;
   said orifices communicating with the duct of said support and duct member; and
   cannulae communicating with said orifices.

19. The injection device according to claim 18, wherein said support and duct member is connected to means for substantially continuously dispensing medicaments.

20. The injection device according to claim 19, wherein:
   said longitudinal axis of said support and duct member is nonrectilinear;
   said support and duct member is arcuate;
   there are more than two said orifices and an equal number of said cannulae;
   said orifices are substantially evenly spaced along said support and duct member;
   said cannulae are substantially evenly spaced from one another;
   said support and duct member is ring-shaped;
   at least one said cannulae is closed at the end remote from its corresponding orifice and such said cannulae contains at least one medicament-transporting duct transverse to its longitudinal axis;
   said cannulae are substantially perpendicular to said longitudinal axis of said support and duct member;
   said support and duct member is provided with a longitudinal connection for connection to said means for continuously dispensing medicament;
   said support and duct member has rigidity to support its own weight;
   said longitudinal connection is tangential with respect to said support and duct member;
   there are at least two medicament transporting ducts;
   said support and duct member is for affixing by affixing means to an area to receive an injection;
   said affixing means comprises physiological compatible cross-plaster bandages; and
   said support and duct member and said longitudinal connection are configured to have a low-profile.

* * * * *